United States Patent

Gronwald et al.

Patent Number: 5,010,074
Date of Patent: Apr. 23, 1991

[54] NOVEL BENZAZEPINE DERIVATIVES

[75] Inventors: Frederik Gronwald, Vedbaek; Peter H. Andersen, Vanlse; Peter Faarup, Vaerlose; Erling Guddal, Brondby; Kristian T. Hansen, Kobenhavn; Louis B. Hansen; Erik B. Nielsen, both of Vaerlose, all of Denmark

[73] Assignee: Novo Nordisk A/S, Bagsvaerd, Denmark

[21] Appl. No.: 365,250

[22] Filed: Jun. 12, 1989

[30] Foreign Application Priority Data

Jun. 15, 1988 [DK] Denmark .............................. 3251/88

[51] Int. Cl.$^5$ .................. C07D 223/14; C07D 223/16; A61K 31/55

[52] U.S. Cl. ..................................... 514/213; 540/576; 540/594; 540/595

[58] Field of Search ................. 540/594, 595; 514/213

[56] References Cited

U.S. PATENT DOCUMENTS 4,210,749 7/1980 Shetty .................................. 540/594
4,327,023 4/1982 Holden et al. ...................... 540/595
4,751,222 6/1988 Braestrup et al. ................... 514/213

FOREIGN PATENT DOCUMENTS 0200455 11/1986 European Pat. Off. .

Primary Examiner—Mukund J. Shah
Assistant Examiner—Philip Dalton
Attorney, Agent, or Firm—Gordon W. Hueschen

[57] ABSTRACT

Novel 2,3,4,5-tetrahydro-1H-3-benzazepines having the formula

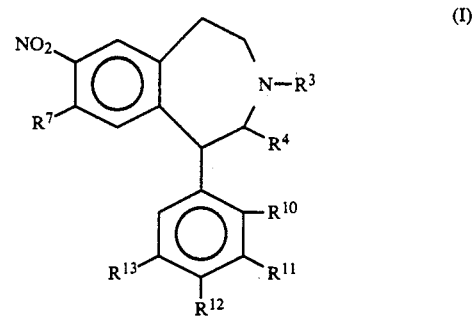

wherein $R^3$ represents H, $C_{1-3}$-alkyl or $C_{3-7}$-cycloalkyl; $R^4$ represents hydrogen or $R^4$ together with $R^{10}$ represents a bridge which connects the positions to which $R^4$ and $R^{10}$ are linked, said bridge being —$CH_2$—$CH_2$—, —CH=CH—, —O—$CH_2$— or —S—$CH_2$—;

$R^7$ represent hydroxy, lower alkoxy;

$R^{10}$, $R^{11}$, $R^{12}$ independently represent hydrogen or halogen or alkyl or alkoxy or trifluoromethyl, or $R^{10}$ together with $R^4$ represents a bridge as described in connection with the definition of $R^4$; or $R^{10}$ together with $R^{11}$ represents a bridge or $R^{11}$ together with $R^{12}$ represents a bridge, the bridge in both cases being chosen among —O—$CH_2$—$CH_2$—, —O—$CH_2$—$CH_2$—$CH_2$—, —O-CH=CH—, —$CH_2$-$CH_2$-$CH_2$—, —$CH_2$-CH=CH— or —$CH_2$—$CH_2$—$CH_2$—;

$R^{13}$ represents hydrogen, halogen or lower alkyl.

The compounds are useful in preparations for treatment of disorders in the central nervous system.

30 Claims, No Drawings

NOVEL BENZAZEPINE DERIVATIVES

This invention relates to novel 2,3,4,5-tetrahydro-1H-3-benzazepines and pharmaceutically acceptable acid addition salt thereof, to methods for their preparation, to pharmaceutical compositions containing them, and to their use in the treatment of certain disorders in the central nervous system.

In the last decade, intensive pharmacological research concerning benzazepines has taken place. The pharmacological properties of benzazepines depend to a large extent on the substituents. For example, substituted benzazepines exhibiting neuroleptic, antiaggressive, antiparkinson and certain vascular effects, are known.

In U.S. patent specification No. 3,393,192 (Schering) derivatives of 5-phenyl-2,3,4,5-tetrahydro-1H-3-benzazepine having, inter alia, hydroxy, lower alkoxy or halogen in the 7- and/or 8-position are described.

In European patent applications publication Nos. 5,298 and 5,299 (Scherico) the corresponding 7-hydroxy derivatives are described.

In European patent application publication No. 200,455 (NOVO) 2,3,4,5-tetrahydro-1H-3-benzazepines having a heterocyclic or an ortho-fused heterocyclic ringsystem in the 5-position are described. These compounds are claimed to have antipsychotic and antidepressive effects.

Furthermore, it has been reported in *Eur.J.Pharmacol.* 91 (1983) 153 et seq., that (R)-8-chloro-7-hydroxy-2,3,4,5-tetrahydro-3-methyl-5-phenyl-1H-3-benzazepine (designated SCH 23390) is a selective D1 dopamine antagonist (see also European patent application publication No. 5,300 (Scherico)).

A common drawback which seriously limits the use of the above-mentioned benzazepines is their low bioavailability after oral administration.

Thus, one object of the present invention is to provide compounds which are dopamine antagonists.

A second object of the present invention is to provide compounds which are useful as neuroleptics.

A third object of the present invention is to provide compounds which can be used for the treatment of various mental disorders, e.g. manic-depressive disorders.

A fourth object of the present invention is to provide substituted benzazepines which have a favourable bioavailability after oral ingestion.

It has now been found that novel 2,3,4,5-tetrahydro-1H-3-benzazepines of the general formula I

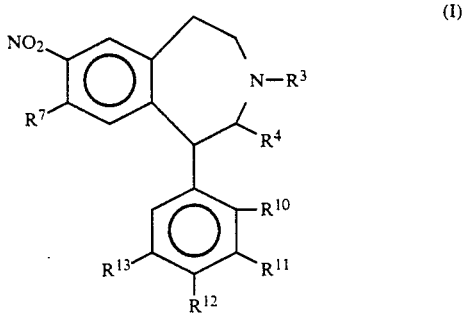

(I)

wherein $R^3$ represents H, $C_{1-3}$-alkyl or $C_{3-7}$-cycloalkyl; $R^4$ represents hydrogen or $R^4$ together with $R^{10}$ represents a bridge which connects the positions to which $R^4$ and $R^{10}$ are linked, said bridge being $-CH_2-CH_2-$, $-CH=CH-$, $-O-CH_2-$ or $-S-CH_2-$; $R^7$ represents hydroxy or lower alkoxy; $R^{10}$, $R^{11}$ and $R^{12}$ independently represents hydrogen, halogen, alkoxy, trifluoromethyl, or alkyl or $R^{10}$ together with $R^4$ represents a bridge as described in connection with the definition of $R^4$; or $R^{10}$ together with $R^{11}$ represents a bridge or $R^{11}$ together with $R^{12}$ represents a bridge, the bridge in both cases being chosen among $-O-CH_2-CH_2-$, $-O-CH_2-CH_2-CH_2-$, $-O-CH=CH-$, $-CH_2-CH_2CH_2-$, $-CH_2-CH=CH-$ or $-CH_2-CH_2-CH_2-$; $R^{13}$ represents hydrogen, halogen or lower alkyl and pharmaceutically acceptable acid addition salts thereof, exhibit useful pharmacological properties, especially on the central nervous system, and that they have a surprisingly favourable bioavailability after oral administration.

DETAILED DISCUSSION OF THE INVENTION

The prior art does not suggest that a particular pharmacological advantage can be expected as a result of the specific substitution pattern present in the structures of the benzazepines of this invention.

The compounds of formula I exhibit a strong antidopaminergic effect. Thus, they potently inhibit stereotyped gnawing behaviour in mice induced by methylphenidate (testing performed as previously described in *Acta Pharmacol. Toxicol.* 31 (1972) 488), and they also inhibit conditioned avoidance response and amphetamine cue in rats.

The benzazepine derivative SCH 23390 has been reported to exhibit a poor bioavailability after oral administration and a short duration of action (*vide Life Sci.* 34 (1984) 1529). The compounds of formula I exhibit a favourable bioavailability.

The compounds of formula I may be present as a mixture of optical isomers which may be resolved into the individual pure isomers. This resolution may conveniently be accomplished by fractional crystallization, from appropriate solvents, of the salts of the compounds of formula I with optically active acids. When the optical isomers are resolved the desired pharmacological activity usually predominates in one of them. Therefore, this invention includes all isomers, whether resolved or mixtures thereof.

Throughout this specification, the term alkyl when used alone or in a combination like alkoxy represents a straight or branched chain with not more than four carbon atoms, for example methyl, ethyl, propyl, isopropyl and tert- butyl. By the term alkoxy is preferably intended methoxy and ethoxy. Halogen is fluoro, chloro, bromo and iodo, preferably chloro and bromo.

According to the above definitions, the substituents designated $R^4$, $R^{10}$, $R^{11}$, and $R^{12}$ may be involved in the formation of bridges. Thus, when $R^4$ forms a bridge together with $R^{10}$ a tetracyclic, ortho-fused ring system is obtained except when $R^{11}$ at the same time forms a bridge together with $R^{12}$ so that a pentacyclic system of ortho-fused ring results.

Particularly valuable embodiments of this invention are nontoxic, pharmaceutically acceptable acid addition salts of benzazepines of formula I. Such salts include those derived from inorganic and organic acids such as hydrochloric, hydrobromic, sulphuric, phosphoric, methane-sulphonic, acetic, lactic, maleic, phthalic and tartaric acids. They may be prepared by standard procedures, such as mixing a solution of the base in acetone or in a lower alcohol with the stoichiometrical amount of the acid in a solvent, such as acetone or a lower alcohol, and evaporating the solvent to leave the desired salt as a residue.

In one group of preferred benzazepines of formula I, $R^3$ is methyl.

In a second group of preferred benzazepines of formula I, $R^4$ is hydrogen or $R^4$ together with $R^{10}$ is a bridge of the formula —O—CH$_2$— which is oriented so that the carbon atom is linked to the benzazepine nucleus or $R^4$ together with $R^{10}$ is a bridge of the formula —CH$_2$—CH$_2$—.

In a third group of preferred benzazepines of formula I, $R^7$ is hydroxy.

In a fourth group of preferred benzazepines of formula I, $R^{10}$ together with $R^{11}$ is a bridge of the formula —O—CH$_2$—CH$_2$— or —O—CH=CH— with the group comprising both possible orientations of the bridges.

In a fifth group of preferred benzazepines of formula I, $R^{10}$ together with $R^{11}$ is a bridge of the formula —O—CH$_2$—CH$_2$—CH$_2$— or —CH$_2$—CH$_2$—CH$_2$—CH$_2$— with the group comprising both possible orientations of the oxygen containing bridge.

In a sixth group of preferred benzazepines of formula I, $R^{10}$ together with $R^{11}$ is a bridge of the formula —CH$_2$—CH$_2$—CH$_2$— or —CH$_2$—CH=CH— with the group comprising both possible orientations of the double bond.

In a seventh group of preferred benzazepines of formula I, $R^{11}$ is hydrogen.

In an eighth group of preferred benzazepines of formula I, $R^{12}$ is hydrogen.

In a nineth group of preferred benzazepines of formula I, $R^{11}$ together with $R^{12}$ is a bridge of the formula —O—CH$_2$—CH$_2$—, —O—CH=CH—, —CH$_2$CH$_2$—CH$_2$— or —CH$_2$—CH=CH— with the group comprising both possible orientations of the asymmetric bridges.

In a tenth group of preferred benzazepines of formula I, $R^{13}$ is hydrogen or chloro.

The 2,3,4,5-tetrahydrobenzazepines of the general formula I can be prepared by one or more of the following methods A-D.

The starting materials for which the preparation is not described herein, are either known compounds or compounds which may be prepared in analogy with the preparation of known compounds or in analogy with known methods.

Method A

Compounds of the general formula III in which

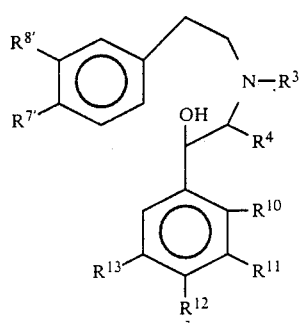

(III)

$R^3$, $R^4$, $R^{10}$, $R^{11}$, $R^{12}$ and $R^{13}$ are as defined for the compounds of the general formula I and $R^{7'}$ is alkoxy and $R^{8'}$ is hydrogen or chloro or bromo can be transformed to benzazepines of formula IV by ring closure in an acidic medium such as sulphuric acid, mixtures of trifluoroacetic acid and sulphuric acid (1-10%) or methanesulphonic acid at temperatures from $-10°$ C. to 50° C. depending on the reaction medium.

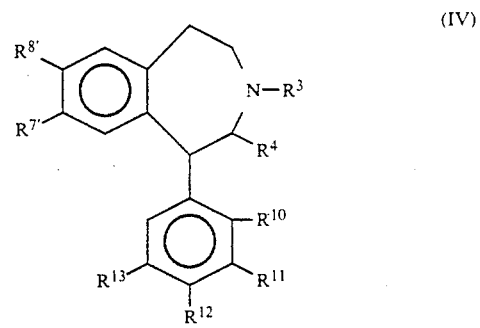

(IV)

This method is analogous to the method described in European patent application publication No. 200,455. All compounds of formula IV can be used as intermediates for the synthesis of benzazepines of formula I.

Method B

Compounds of the general formula IV in which $R^{8'}$ is halogen and $R^{7'}$ is hydroxy or alkoxy and the rest of the substituents are as defined above can be dehalogenated in the 8-position by catalytic hydrogenation e.g. palladium on carbon, as well at atmospheric pressure as at elevated pressure. Also, other halogens optionally present in the starting material may at the same time, depending on the specific compound and on the reaction conditions, be exchanged with hydrogen.

The solvents preferred are water at high pH (pH 9-13) or dimethylformamide or acetic acid and sodium acetate, however, other solvents may also be used. The dehalogenated compounds have the general formula V

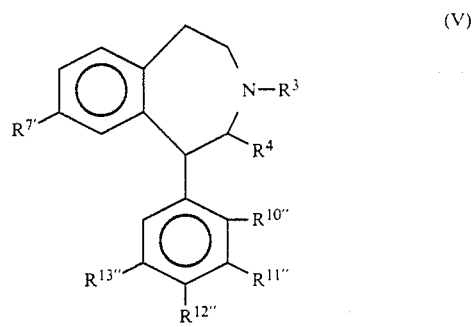

(V)

in which the substituents $R^3$, $R^4$ and $R^{7'}$ are as defined above and the substituents $R^{10''}$, $R^{11''}$, $R^{12''}$ and $R^{13''}$ each are identical independently representing hydrogen, alkyl or alkoxy, except that where an optional further halogen in the starting material has been exchanged with hydrogen the corresponding double primed substituent in formula V designates hydrogen.

Method C

Compounds of the general formula V in which $R^{7'}$ is hydroxy or alkoxy, with the proviso when $R^3$ is hydrogen the amine has to be protected by acylation, can be nitrated by generally known methods (see, for example, Jerry March: *Advanced Organic Chemistry* 3rd ed., McGraw-Hill, New York, 1985) e.g. by treating a solution of a compound of the general formula V in acetic acid or in a mixture of acetic acid and methylene chloride with fuming nitric acid at temperatures from $-10°$ C. to $10°$ C. The products obtained will predominantly be mononitrated with the nitro group in the 8-position. In case $R^3$ is hydrogen the protected amine can be converted to a compound of formula V by deacylation per se.

The nitrated compounds can be used as such for therapeutic purposes or as intermediates for the synthesis of other benzazepines.

Method D

Compounds of the general formula IV or V in which the substituent $R^{7'}$ is alkoxy can be O-dealkylated by generally known methods to yield the corresponding 7-hydroxy compounds, for example by treating a solution of the substrate in methylene chloride with boron tribromide at low temperature, e.g. $-70°$ C. to $30°$ C., preferably $-25°$ C. to $0°$ C. (see, for example, Theodora W. Greene: *Protective Groups in Organic Synthesis*, John Wiley, New York, 1981).

In some cases the succession of the reactions may be different from the one described here. For example the O-dealkylation may be carried out before the nitration.

The benzazepines of formula I are useful because of their pharmacological activity. In particular, the compounds of formula I can be useful as antipsychotics. The benzazepines of formula I are administered in an effective amount to a host in need of treatment.

Compounds of formula I were tested for their binding to dopamine D1 receptor in homogenates from rat striatum using the method described (Life Science vol. 37, p. 1971 (1985) P. Andersen et. al.) and the results appear from table I, where the compounds of formula I tested are the (+) enantiomere or racemic mixtures. $K_i$ is the affinity of tested compounds for the dopamine D1 receptor.

TABLE I

| Test Compound | $K_i$ nM Dopamine D1 receptor |
|---|---|
| Example 1 | 42 |
| Example 3 | 28 |
| Example 4 | 13 |
| Example 5 | 11 |
| Example 6 | 88 |
| Example 7 | 169 |

As already mentioned, the benzazepines of the general formula given in Table II with X representing halogen have a low oral bioavailability. The increased bioavailability of the benzazepines according to the present invention compared to the corresponding benzazepines wherein X is halogen can be demonstrated either by comparing the ratio between the $ED_{50}$ by peroral and intraveneous administration in inhibiting amphetamine in rats or by comparing the absolute oral bioavailability for the compounds in question as measured in mongrel dogs. Some test results are stated in the following.

PHARMACOLOGICAL EXPERIMENTS

Following the method of Pedersen, V. and Christensen, A.V.: "Antagonism of methylphenidate-induced stereotyped gnawing in mice", Acta Pharmacol. et Toxicol. 31: 488–496, 1972, antagonism of dopamine-dependent, methyl-phenidate-induced gnawing behaviour of mice, was used to assess the effects of the present D-1 antagonists. Further, the ratio of $ED_{50}$ values obtained using i.v. administration and oral administration, respectively, was taken as an index of the bioavailability of the test drugs. It was found that the presence of a nitrogroup in the 8th position plays a crucial role for the p.o./i.v. effect ratio and, hence, for the bioavailability.

The following values were obtained:

TABLE II

|  |  | $K_i$ | $ED_{50}$-values (mg/kg) p.o. | i.v. | Ratio p.o./i.v. |  |
|---|---|---|---|---|---|---|
| X = Cl | R = phenyl | 0.14 | 6.5 | 0.017 | 382 | (1) |
| X = NO$_2$ | R = phenyl | 13 | 11.9 | 5.4 | 2.2 | (2) |
| X = Cl | R = benzofuranyl | 0.2 | 4.5 | 0.06 | 75 | (3) |

TABLE II-continued

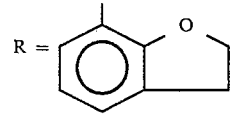

| | $K_i$ | ED$_{50}$-values (mg/kg) p.o. | i.v. | Ratio p.o./i.v. | |
|---|---|---|---|---|---|
| X = NO$_2$ R = [benzofuran] | 4.6 | 1.9 | 0.11 | 17.3 | (4) |

(1) Reference substance SCH 23390
(2) Compound of example 4
(3) Reference substance, compound g of example 5 in U.S. Pat. No. 4,751,222 (NOVO)
(4) Compound of example 5

Investigation of Absolute Bioavailability

The benzazepines are administered orally to dogs and subsequently samples of their blood plasma are analysed for the compound by a specific HPLC-method. The area under the curve showing the oral plasma concentration versus time is calculated. This area is designated AUC i.v.

The absolute oral bioavailability, F, is calculated as the ratio between the area representing the oral dose and the area for the intravenous dose according to the formula $$F = \frac{AUC \text{ p.o.}/\text{dose p.o.} \times 100}{AUC \text{ i.v.}/\text{dose i.v.}}$$

The results are shown in Table III.

TABLE III

| Substance | Absolute bioavailability, F (%) F (%) |
|---|---|
| 8-chloro-7-hydroxy-3-methyl-5-(2,3-dihydro-benzofuran-7-yl)-2,3,4,5-tetrahydro-1H-3-benzazepine (note 1) | 5.5 |
| (+)-7-hydroxy-3-methyl-8-nitro-5-(2,3-dihydro-benzofuran-7-yl)-2,3,4,5-tetrahydro-1H-3-benzazepine (note 2) | 65 | note 1:
reference substance, compound g of example 5 in U.S. Pat. No. 4,751,222 (NOVO)
note 2:
the compound according to example 5 of the present specification The acute toxicity of the compounds investigated is low.

The dosage of the compounds of the invention when employed in therapy will depend on the particular benzazepine of formula I in question on the mode of administration and on the therapy desired. However, in general, satisfactory results may be obtained with a daily dosage of from 0,005 mg to about 5 mg per kg body weight, conveniently given in divided doses 2 to 5 times a day or in sustained release form. Usually, dosage forms suitable for oral administration comprise from about 0.5 mg to about 250 mg of the benzazepine of formula I admixed with a pharmaceutical carrier or diluent.

The benzazepines of formula I may be administered in the form of a pharmaceutically acceptable acid addition salt. The invention also relates to pharmaceutical compositions comprising a benzazepine of formula I or a pharmaceutically acceptable salt thereof and, usually, such compositions also contain a pharmaceutical carrier or diluent. The compositions of this invention may be prepared by conventional techniques to be in conventional forms, for example, capsules or tablets.

The pharmaceutical carriers employed can be conventional solid or liquid carriers. Examples of solid carriers are lactose, terra alba, sucrose, talc, gelatin, agar, pectin, acacia, magnesium stearate and stearic acid. Examples of liquid carriers are syrup peanut oil olive oil and water. Similarly, the carrier or diluent may include any time delay material well known to the art, such as glyceryl monostearate or glyceryl distearate alone or together with a wax.

If a solid carrier for oral administration is used, the preparation can be tableted, placed in a hard gelatin capsule in powder or pellet form or in the form of a troche or lozenge. The amount of solid carrier will vary widely but will usually be frOm abOut 25 mg to about 1 g. If a liquid carrier is used, the preparation may, for example, be in the form of a syrup, an emulsion, a soft gelatin capsule, a sterile, injectable solution or an aqueous or non-aqueous liquid suspension.

The pharmaceutical compositions of this invention may be made following the conventional techniques of the pharmaceutical chemist involving mixing, granulating and compressing or variously mixing and dissolving the ingredients as appropriate to give the desired end product.

The route of administration may be any route which effectively transports the active compound to the desired place, such as oral or parenteral, the oral route being preferred.

The nomenclature used herein on the whole complies with the IUPAC nomenclature, one of the main deviations being that in an attempt to facilitate the reading of this specification, herein the position of the benzazepine nucleus to which the phenyl group carrying the substituents $R^{10}$-$R^{13}$ is linked is always designated number 5. According to the IUPAC nomenclature this position has the number 1 or 5, depending on the further substituents in the benzazepine nucleus. Further, in order to facilitate the comparison of different series of substitution patterns the substituents are not always arranged in alphabetical order in the names of the compounds.

The features disclosed in the foregoing description and in the following examples and claims may, both separately and in any combination thereof, be material for realizing the invention in diverse forms thereof.

The invention is further illustrated by the following examples which, however, are not to be construed as limiting.

The starting material for which the preparation is not desribed herein is described in European Patent Application publication No. 200,455 (NOVO) and in European Patent Application publication No. 023 0270.

EXAMPLE 1

5-(2-fluorophenyl)-7-hydroxy-3-methyl-8-nitro-2,3,4,5-tetrahydro-1H-3-benzazepine (A) 5-(2-fluorophenyl)-7-hydroxy-3-methyl-2,3,4,5-tetrahydro-1H-3-benzazepine:

10.0 g 8-chloro-5-(2-fluorophenyl)-7-hydroxy-3-methyl-2,3,4,5-tetrahydro-1H-3-benzazepine was dissolved in 500 ml acetic acid containing sodium acetate. Palladium-on-carbon was added and the suspension was heated to 60° C. Under vigorous stirring hydrogen was led through the suspension giving after 48 h 7,9 g crystalline compound. Yield 72%.

NMR: >CH—OH 4,45 dd, $C_6H$ 5,95 d, $C_8H$ 6,45 d, $C_7OH$ 8,75 s ppm. respectively.

This compound was used for the next step without further purification.

(B) 5-(2-fluorophenyl)-7-hydroxy-3-methyl-8-nitro-2,3,4,5-tetrahydro-1H-5-benzazepine:

5.0 g 5-(2-fluorophenyl)-7-hydroxy-3-methyl-2,3,4,5-tetrahydro-1H-3-benzazepine was dissolved in 90 ml of a mixture of acetic acid and cooled in ice-water bath 0° C. Under stirring was added 1,7 ml fuming nitric acid and the mixture was stirred in the cold for 1 h. The reaction mixture was neutralized (pH 7.9) and the precipitate was extracted with ethyl acetate, dried and evaporated. After column chromatography (kieselgel/$CH_2Cl_2$: $CH_3OH$ 95: 5) was isolated yellow crystals. M.p. 90°-94° C. (dec). NMR: $C_5\underline{H}$ 4.61d $C_6\underline{H}$ g 41% 6 s and $C_9\underline{H}$ 7.88 s ppm. respectively.

EXAMPLE 2

7-hydroxy-3-methyl-8-nitro-5-(3-trifluoromethyl-phenyl)-2,3,4,5-tetrahydro-1H-3-benzazepine (A) 7-hydroxy-3-methyl-5-(3-trifluoromethylphenyl)-2,3,4,5-tetrahydro-1H-3-benzazepine was prepared in analogy with the method A in example 1. Yield 2,5 g, 81%. NMR: $C_5\underline{H}$ 4,25 dd: $C_6\underline{H}$ 5,9d: $C_8\underline{H}$ 6,5 dd; $C_9\underline{H}$ 7,0 d ppm. respectively.

This compound was used for the next step without further purification.

(B) 7-hydroxy-3-methyl-8-nitro-(3-trifluoromethylphenyl)-2,3,4,5-tetrahydro-1H-3-benzazepine is prepared in analogy with method B in example 1 giving 0.4 g (14%). M.p. 205°-210° C. (dec). NMR: $C_5\underline{H}$ 5,08d: $C_6\underline{H}$ 6,5 s: $C_9\underline{H}$ 7.88s ppm. respectively.

EXAMPLE 3

7-hydroxy-3-methyl-8-nitro-5(2-methyl-phenyl)-2,3,4 5-tetrahydro-1H-3-benzazepine (A) 1 g of 7-methoxy-3-methyl-5-(2-methyl-phenyl)-2,3,4,5-tetrahydro-1H-3-benzazepine was dissolved in a mixture of acetic acid (5 ml) and acetic anhydride (5 ml). To this mixture was added fuming nitric acid and the reaction mixture was stirred at room temperature for 2 h. Crushed ice was added to the reaction mixture and sodium hydroxide solution (6 N) was added slowly to pH 7.5. This mixture was extracted with ethyl acetate, the combined organic layer was dried and evaporated giving a solid which was purified by column chromatography (kieselgel: $CH_2Cl_2/CH_3OH$ 98/2). Yield: 300 mg (27%). NMR: $C_5\underline{H}$ 4.58d: $C_6\underline{H}$ 6.11s: $C_9\underline{H}$ 7.64s ppm. respectively.

This compound was used directly for the next step.

(B) 300 mg 7-methoxy-3-methyl-8-nitro-5(2'-methyl-phenyl)-2,3,4,5-tetrahydro-1H-3-benzazepine was dissolved in MeOH and cooled to −70° C. 1 g $BBr_3$ was added slowly and the mixture was stirred for 1 h at −70° C., and stirring was continued for 1 h. Methanol was slowly added to distroy the excess of $BBr_3$ and the mixture was evaporated to dryness. The raw material was purified by column chromatography (kieselgel, $CH_2Cl_2/CH_3OH$: 98/2) giving 110 mg of the desired compound. M.p. 59°-61° C. NMR: $C_5\underline{H}$ 5.10d: $C_6\underline{H}$ 6.20S: $C_9\underline{H}$ 8.05s ppm. respectively.

EXAMPLE 4

(R)-7-hydroxy-3-methyl-8-nitro-5-phenyl-2,3,4,5-tetrahydro-1H-3-benzazepine (R)-7-hydroxy-3-methyl-5-phenyl-2,3,4,5-tetrahydro-1H-3-benzazepine was prepared in analogy with the method described in example 1B giving 1.5 g (42%). M.p. 90°-92 ° C. NMR: $C_5\underline{H}$ 4.37d: $C_6\underline{H}$ 6.46s: $C_9\underline{H}$ 7.88s ppm. respectively.

EXAMPLE 5

(+)-5-(2,3-dihydrobenzofuran-7-yl)-7-hydroxy-3-methyl-8-nitro-2,3,4,5-tetrahydro-1H-3-benzazepine (A) (+)-5-(2,3-dihydrobenzofuran-7-yl)-7-hydroxy-3-methyl-2,3,4,5-tetrahydro-1H-3-benzazepine 6.55 g, (0.020 mol) (+)-5-(benzofuran-7-yl)-8-chloro-7-hydroxy-3-methyl-2,3,4,5-tetrahydro-1H-3-benzazepine was dissolved in 1.0 N sodium hydroxide (100 ml, 0.100 mol) and water (100 ml). 10% palladium-on-carbon (3.0 g) was added, and the resulting suspension was stirred under hydrogen at 20° C. and 100 kPa for 5 days. The reaction mixture was filtered and the filtercake was thoroughly washed with 0.3 N hydrochloric acid (70 ml) and methanol (135 ml). The pH of the combined filtrate and washings was brought to 8.0 and the resulting suspension was filtered. The filtercake was washed with water/methanol (1/1) and dried in vacuo at 40° C. to give 3.45 g (76% of the theoretical yield) of the desired compound as white crystals.) M.p. 227°-30° C.

(B) 3.0 g (3.03 mmol) (+)-5-(2,3-dihydrobenzofuran-7-yl)-7-hydroxy-3-methyl-2,3,4,5-tetrahydro-1H-3-benzazepine was dissolved in a mixture of methylene chloride (25 ml) and acetic acid (75 ml) at 10° C. and fuming nitric acid (0.5 ml) was added. The reaction mixture was stirred for 2 h at 10°-15° C. Then the reaction mixture was evaporated to about 20 ml and diluted with water (100 ml). pH was adjusted to 8.5 and the water phase was extracted twice with methylene chloride. The combined organic phases were dried and evaporated to give 2.1 g of crude product.

Purification by column chromatography (methylene chloride/methanol 9/1) gave 1.9 g of (+)-5-(2,3-dihydrobenzofuran-7-yl)-7-hydroxy-3-methyl-8-nitro-2,3,4,5-tetrahydro-1H-3-benzazepine as white crystals. M.p. 122°-3° C.

Calc.: 67.0% C, 5.9% H, 8.2% N.

Found: 66.8% C, 6.1% H, 8.1% N.

EXAMPLE 6

7-hydroxy-5-(5-indanyl)-3-methyl-8-nitro-2,3,4,5-tetrahydro-1H-3-benzazepine (A) 7-hydroxy-5-(5-indanyl)-3-methyl-2,3,4,5-tetrahydro-1H-3-benzazepine was prepared in analogy with example 1 A. Yield: 1.05 g (92%). M.p. 213°–22° C. (dec). NMR: $C_5\underline{H}$ 4.6d: $C_6\underline{H}$ 5.65d: $C_8\underline{H}$ 6.4dd: $C_9\underline{H}$ 6.9d ppm. respectively.

(B) 7-hydroxy-5-(5-indanyl)-3-methyl-8-nitro-2,3,4,5-tetrahydro-1H-3-benzazepine was prepared in analogy with example 1B. Yield: 0.45 g (39%). M.p. 58°–63° C. NMR: $C_5\underline{H}$ 4.66d: $C_6\underline{H}$ 6.06s, $C_9\underline{H}$ 7.8s ppm. respectively.

Calc.: 70.99% C, 6.55% H, 7.67% N.
Found: 70.43% C, 6.94% H, 7.77% N.

EXAMPLE 7 trans-[6,7,7a,8,9,13b]-hexahydro-2-hydroxy-7-methyl-3-nitro-5H-benzo[d]naphto[2,1-b]azepine trans-[6,7,7a,8,9,13b]-hexahydro-2-hydroxy-7-methyl-5H-benzo[d]naphto[2,1-b]azepine (642 mg) was dissolved in a mixture of 40 ml acetic acid and 4 ml of water, cooled to about 5° C. and treated with 0.5 ml of concentrated nitric acid. After 1 h the reaction mixture was neutralized to pH 7.8. The precipitate was collected and purified by column chromatography (silicagel; THF+1% TEA) giving 95 mg (15% th). M.p. 115°–20° C. NMR: $C_1H$: 6.06 s: $C_4H$ 7.8s: $C_{13b}H$ 4.75d ppm. respectively.

EXAMPLE 8

Preparation of Capsules

| Ingredients | mg per capsule |
|---|---|
| (+)-7-hydroxy-3-methyl-8-nitro-5-(2,3-dihydrobenzofuran-7-yl)-2,3,4,5-tetrahydro-1H-3-benzazepine hydrobromide | 125 |
| magnesium stearate | 2 |
| lactose | 200 |

The above ingredients were thoroughly mixed and placed into hard gelatin capsules. Such capsules were administered orally to subjects in need of treatment one or more times daily.

EXAMPLE 9

Preparation of Tablets

| Ingredients | mg per tablet |
|---|---|
| (+)-7-hydroxy-3-methyl-8-nitro-5-(2,3-dihydrobenzofuran-7-yl)-2,3,4,5-tetrahydro-1H-3-benzazepine hydrobromide | 200 |
| corn starch | 46 |
| polyvinyl pyrrolidone | 12 |
| magnesium stearate | 1 |

The benzazepine was thoroughly mixed with two thirds of the corn starch and granulated. The granules obtained were dried, mixed with the remaining ingredients and compressed into tablets.

We claim:

1. A 2,3,4,5-tetrahydro-1H-3-benzazepine selected from those of the formula I

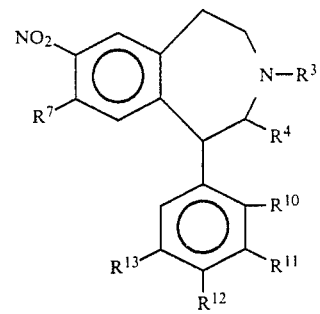

wherein $R^3$ represents $C_{1-3}$-alkyl or $C_{3-7}$-cycloalkyl; $R^4$ represents hydrogen; $R^7$ represents hydroxy or lower alkoxy; one of $R^{10}$, $R^{11}$, $R^{12}$ and $R^{13}$ represents trifluromethyl and the others independently represent hydrogen or $R^{11}$ together with either $R^{10}$ or $R^{12}$ represents a bridge chosen from among —O—CH$_2$—CH—, —O—CH$_2$—CH$_2$—CH$_2$—, —O—CH=CH—, —CH$_2$—CH$_2$—CH$_2$—, —CH$_2$—CH=CH— and —CH$_2$—CH$_2$—CH$_2$—, and the remainder of $R^{10}$, $R^{11}$, $R^{12}$ and $R^{13}$ each represents hydrogen, and pharmaceutically-acceptable acid additional salts thereof.

2. Benzazepine according to claim 1 wherein $R^7$ is hydroxy.

3. Benzazepine according to claim 2 wherein $R^4$ is hydrogen and $R^{10}$ and $R^{11}$ represent a bridge, said bridge being —O—CH$_2$—CH$_2$— or —O—CH=CH— or —CH$_2$—CH=CH— or —CH$_2$—CH$_2$—CH$_2$—.

4. Benzazepine according to claim 3 wherein $R^{12}$ and $R^{13}$ represent hydrogen.

5. Benzazepine according to claim 2 wherein $R^{12}$ and $R^{13}$ represent hydrogen.

6. Benzazepine according to claim 1 wherein $R^4$ is hydrogen and $R^{10}$ and $R^{11}$ represent a bridge, said bridge being —O—CH$_2$—CH$_2$— or —O—CH=CH— or —CH$_2$—CH=CH— or —CH$_2$—CH$_2$—CH$_2$—.

7. Benzazepine according to claim 6 wherein $R^{12}$ and $R^{13}$ represent hydrogen.

8. Benzazepine according to claim 1 wherein $R^{12}$ and $R^{13}$ represent hydrogen.

9. A compound according to claim 1 which is (+)-7-hydroxy-3-methyl-8-nitro-5-(2,3-dihydro-benzofuran-7-yl)-2,3,4,5-tetrahydro-1H-3-benzazepine.

10. A compound according to claim 1 which is 7-hydroxy-3-methyl-8-nitro-5-(3-trifluoromethylphenyl)-2,3,4,5-tetrahydro-1H-3-benzazepine.

11. A compound according to claim 1 wherein the substituent in the 5 position of the benzazepine nucleus is 2,3-dihydrobenzofuranyl-7-yl.

12. A compound according to claim 1 wherein the substituent in the 5 position of the benzazepine nucleus is 5-indanyl.

13. A compound according to claim 1 which is 7-hydroxy-5-(5-indanyl)-3-methyl-8-nitro-2,3,4,5-tetrahydro-1H-3-benzazepine.

14. A pharmaceutical composition useful for treating CNS ailments containing an effective amount of a benzazepine of claim 1 or a pharmaceutically-acceptable acid addition salt thereof together with a pharmaceutically-acceptable carrier or diluent.

15. A pharmaceutical composition according to claim 14, which contains between 0.1 mg and 250 mg of the active ingredient or a pharmaceutically acceptable acid addition salt thereof per dose unit.

16. A method of treating a central nervous system ailment sensitive to the dopamine D1 receptor comprising the step of administering to the said subject an effective amount of a compound having the formula I:

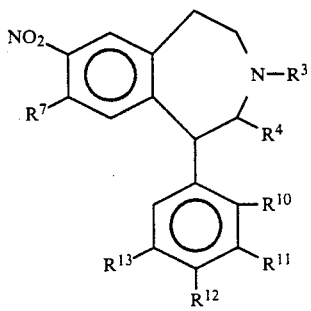

wherein $R^3$ represents $C_{1-3}$-alkyl or $C_{3-7}$-cycloalkyl; $R^4$ represents hydrogen;

$R^7$ represents hydroxy or lower alkoxy;

$R^{10}$, $R^{11}$, $R^{12}$ independently represent hydrogen, halogen, or trifluoromethyl, alkyl, or alkoxy; or $R^{10}$ together with $R^{11}$ represents a bridge or $R^{11}$ together with $R^{12}$ represents a bridge, the bridge in both cases being chosen from among —O—CH$_2$—CH—, —O—CH$_2$—CH$_2$—CH$_2$—, —O—CH=CH—, —CH$_2$CH$_2$—CH$_2$—, —CH$_2$—CH=CH— or —CH$_2$—CH$_2$—CH$_2$—CH$_2$—; and wherein $R^{13}$ represents hydrogen, halogen, or lower alkyl, or a pharmaceutically-acceptable acid-addition salt thereof.

17. A method according to claim 16 wherein the ailment is schizophrenia or manic-depressive disorders.

18. A method according to claim 16 wherein the substituent in the 5 position of the benzazepine nucleus is 2,3-dihydrobenzofuranyl-7-yl.

19. Method according to claim 16 wherein $R^7$ is hydroxy.

20. Method according to claim 19 wherein $R^4$ is hydrogen and $R^{10}$ and $R^{11}$ represent a bridge, said bridge being —O—CH$_2$—CH$_2$— or —O—CH=CH— or —CH$_2$—CH=CH— or —CH$_2$—CH$_2$—CH$_2$—.

21. Method according to claim 19 wherein $R^{12}$ and $R^{13}$ represent hydrogen.

22. Method according to claim 16 wherein $R^4$ is hydrogen and $R^{10}$ and $R^{11}$ represent a bridge, said bridge being —O—CH$_2$—CH$_2$— or —O—CH=CH— or —CH$_2$—CH=CH— or —CH$_2$—CH$_2$—CH$_2$—.

23. Method according to claim 22 wherein $R^{12}$ and $R^{13}$ represent hydrogen.

24. Method according to claim 16 wherein $R^{12}$ and $R^{13}$ represent hydrogen.

25. Method according to claim 16 wherein the compound is (+)-7-hydroxy-3-methyl-8-nitro-5-(2,3-dihydrobenzofuran-7-yl)-2,3,4,5-tetrahydro-1H-3-benzazepine.

26. Method of claim 16 wherein the compound is 5-(2-fluorophenyl-7-hydroxy-3-methyl-8-nitro-2,3,4,5-tetrahydro-1H-3-benzazepine.

27. Method of claim 16 wherein the compound is 7-hydroxy-3-methyl-8-nitro-5-(3-trifluoromethylphenyl)-2,3,4,5-tetrahydro-1H-3-benzazepine.

28. Method of claim 16 wherein the compound is 7-hydroxy-3-methyl-8-nitro-5-(2-methylphenyl)-2,3,4,5-tetrahydro-1H-3-benzazepine.

29. Method of claim 16 wherein the compound is (R)-7-hydroxy-3-methyl-8-nitro-5-phenyl-2,3,4,5-tetrahydro-1H-3-benzazepine.

30. Method of claim 16 wherein the compound is 7-hydroxy-5-(5-indanyl)-3-methyl-8-nitro-2,3,4,5-tetrahydro-1H-3-benzazepine.

* * * * *

UNITED STATES PATENT AND TRADEMARK OFFICE
CERTIFICATE OF CORRECTION

PATENT NO. : 5,010,074
DATED : April 23, 1991
INVENTOR(S) : Frederik Gronwald, Peter H. Andersen, Peter Faarup, Erling Guddal, Kristian T. Hansen, Louis B. Hansen, Erik B. Nielsen It is certified that error appears in the above-identified patent and that said Letters Patent is hereby corrected as shown below:

Title Page, [75] Inventors:, line 2; "Vanlse;" should read -- Vanløse --

Title Page, Assistant Examiner; "Dalton" should read -- Datlow --

Title Page, [57] ABSTRACT, 7th line after the formula; "represent" should read -- represents --

Col. 2, line 11; "—$CH_2CH_2$—," should read -- —$CH_2$—$CH_2$—, --

Col. 2, line 12; "—$CH_2$—;" should read -- —$CH_2$—$CH_2$—; --

Col. 2, line 12; after "halogen" insert a comma -- , --

Col. 2, line 13; after "alkyl" insert a comma -- , --

Col. 7, line 57; after "question" insert a comma -- , --

Col. 8, line 44; "frOm abOut" should read -- from about --

Col. 9, line 11; "desribed" should read -- described --

Col. 9, line 41; "/$CH_2CH_2$:" should read -- /$CH_2Cl_2$: --

Col. 9, line 42; 4.61d" should read -- 4.61d; --

Col. 9, line 63; "-5(2-" should read -- -5-(2- --

Col. 10, line 16; "distroy" should read -- destroy --

UNITED STATES PATENT AND TRADEMARK OFFICE
CERTIFICATE OF CORRECTION

PATENT NO. : 5,010,074

DATED : April 23, 1991      Page 2 of 2

INVENTOR(S) : Frederik Gronwald, Peter H. Anderson, Peter Faarup, Erling Guddal, Kristian T. Hansen, Louis B. Hansen, Erik B. Nielsen It is certified that error appears in the above-identified patent and that said Letters Patent is hereby corrected as shown below:

Col. 2, lines 10 & 11;           ) "—CH—
Col. 2, lines 11 & 12;           )  $_2$" has been hyphenated
Col. 3, lines 22 & 23;           ) incorrectly in all 8 instances.
Col. 12, lines 21 & 22;          ) Correct this hyphenated formula
Col. 12, lines 22 & 23;          ) to read as follows:
Title Page, [57] ABSTRACT,       ) — —CH$_2$— —   (Please make this
   lines 7 & 6 from the bottom;  )
Title Page [57] ABSTRACT,        ) correction in all 8 instances)
   lines 6 & 5 from the bottom; and)
Title Page [57] ABSTRACT,        )
   lines 5 & 4 from the bottom.  )

Col. 3, lines 36 & 37;  "—CH$_2$C-
                              H$_2$"  is hyphenated incorrectly. Correct this hyphenated formula as follows:  — —CH$_2$CH$_2$— —

Signed and Sealed this

Twenty-fourth Day of November, 1992

*Attest:*

DOUGLAS B. COMER

*Attesting Officer*        *Acting Commissioner of Patents and Trademarks*

UNITED STATES PATENT AND TRADEMARK OFFICE
CERTIFICATE OF CORRECTION

PATENT NO. : 5,010,074

DATED : Apr. 23, 1991

INVENTOR(S) : Frederik Gronwald, Peter H. Andersen, Peter Faarup, Erling Guddal, Kristian T. Hansen, Louis B. Hansen, Erik B. Nielsen It is certified that error appears in the above-identified patent and that said Letters Patent is hereby corrected as shown below:

Column 12, line 20; "$-O-CH_2-CH-$," should read -- $-O-CH_2-CH_2-$, --.

Column 13, lines 30,31; "$-O-CH_2-CH-$," should read -- $-O-CH_2-CH_2-$,--.

Title Page, Column 1, Assistant Examiner; "Philip Dalton" should read -- Philip Datlow --.

Column 12, approximately line 25; "additional" should read -- addition --.

Signed and Sealed this

Twenty-eighth Day of September, 1993

Attest:

BRUCE LEHMAN

Attesting Officer

Commissioner of Patents and Trademarks